United States Patent
Pan

(10) Patent No.: US 11,580,893 B2
(45) Date of Patent: Feb. 14, 2023

(54) LUMINANCE CALIBRATION SYSTEM AND METHOD OF MOBILE DEVICE DISPLAY FOR MEDICAL IMAGES

(71) Applicant: EBM TECHNOLOGIES INCORPORATED, Taipei (TW)

(72) Inventor: William Pan, Taipei (TW)

(73) Assignee: EBM TECHNOLOGIES INCORPORATED, Taipei (TW)

( * ) Notice: Subject to any disclaimer, the term of this patent is extended or adjusted under 35 U.S.C. 154(b) by 0 days.

(21) Appl. No.: 16/826,280

(22) Filed: Mar. 22, 2020

(65) Prior Publication Data

US 2021/0248948 A1 Aug. 12, 2021

(30) Foreign Application Priority Data

Feb. 10, 2020 (TW) ................................. 109104057

(51) Int. Cl.
*G09G 3/20* (2006.01)
*G16H 30/40* (2018.01)

(52) U.S. Cl.
CPC ............ *G09G 3/2007* (2013.01); *G16H 30/40* (2018.01); *G09G 2320/0693* (2013.01); *G09G 2360/145* (2013.01); *G09G 2380/08* (2013.01)

(58) Field of Classification Search
CPC ......... G09G 3/2007; G09G 2320/0693; G09G 2360/145; G09G 2380/08; G09G 2320/0233; G09G 3/006; G16H 30/40; G16H 30/20
See application file for complete search history.

(56) References Cited

U.S. PATENT DOCUMENTS

| | | | |
|---|---|---|---|
| 8,519,956 B2 | 8/2013 | Rust | |
| 8,872,924 B1* | 10/2014 | Lin | G06F 3/1446 348/181 |
| 8,890,906 B2 | 11/2014 | Holmes | |
| 10,130,312 B2* | 11/2018 | Hwang | A61B 5/748 |

(Continued)

FOREIGN PATENT DOCUMENTS

| | | |
|---|---|---|
| CN | 104363445 B | 8/2016 |
| CN | 107316593 A | 11/2017 |

(Continued)

*Primary Examiner* — Jose R Soto Lopez
(74) *Attorney, Agent, or Firm* — Winston Hsu

(57) ABSTRACT

A luminance calibration system and method of mobile device display for medical images is provided, and allows a mobile device display to display the medical images complying with grayscale standard display function (GSDF) defined by Digital Imaging and Communications in Medicine (DICOM) under any environmental light sources; for example, the medical images displayed by the mobile device display can meet a Just-Noticeable Difference (JND) defined by DICOM to facilitate medical diagnosis for medical staffs. In addition, the luminance calibration system and method of mobile device display for medical images only adjusts the medical images inside the operating window of the mobile device display, while any image outside the operating window of the mobile device display is reserved; as a result, the luminance calibration system and method of mobile device display for medical images makes the mobile device display to be a medical image screen as well as a regular screen.

7 Claims, 5 Drawing Sheets

(56) References Cited

U.S. PATENT DOCUMENTS

| | | | |
|---|---|---|---|
| 10,607,566 B2* | 3/2020 | Nagashima | G09G 5/04 |
| 2003/0142883 A1* | 7/2003 | Ishii | G06T 3/0068 |
| | | | 382/284 |
| 2004/0140982 A1* | 7/2004 | Pate | H04N 9/3182 |
| | | | 345/600 |
| 2004/0165068 A1* | 8/2004 | Jane | H04N 9/3182 |
| | | | 348/E9.027 |
| 2005/0068291 A1* | 3/2005 | Coley | G09G 5/10 |
| | | | 345/156 |
| 2005/0103976 A1* | 5/2005 | Ioka | H04N 5/74 |
| | | | 348/E17.005 |
| 2006/0028462 A1* | 2/2006 | Ono | G09G 5/003 |
| | | | 345/204 |
| 2006/0208980 A1* | 9/2006 | Okumura | G09G 3/20 |
| | | | 345/87 |
| 2006/0238832 A1* | 10/2006 | Ohsawa | G09G 5/02 |
| | | | 358/518 |
| 2007/0067124 A1* | 3/2007 | Kimpe | G09G 3/2092 |
| | | | 702/67 |
| 2007/0097213 A1* | 5/2007 | Ajito | G09G 3/001 |
| | | | 348/383 |
| 2007/0115361 A1* | 5/2007 | Bolas | H04N 5/74 |
| | | | 348/189 |
| 2007/0177779 A1* | 8/2007 | Dennison | G06T 5/009 |
| | | | 382/128 |
| 2007/0236517 A1* | 10/2007 | Kimpe | G09G 3/2092 |
| | | | 345/690 |
| 2007/0274586 A1* | 11/2007 | Yamano | H04N 1/644 |
| | | | 382/128 |
| 2008/0089572 A1* | 4/2008 | Yamano | A61B 6/461 |
| | | | 348/E9.054 |
| 2009/0115686 A1* | 5/2009 | Ryou | G09G 5/02 |
| | | | 345/2.1 |
| 2009/0115915 A1* | 5/2009 | Steinberg | H04N 9/3194 |
| | | | 353/121 |
| 2009/0141121 A1* | 6/2009 | Kimpe | H04N 13/327 |
| | | | 348/E13.001 |
| 2009/0262341 A1* | 10/2009 | Konopa | G01N 21/95607 |
| | | | 382/141 |
| 2010/0194777 A1* | 8/2010 | Yamano | H04N 1/465 |
| | | | 382/165 |
| 2012/0062621 A1* | 3/2012 | Miyahara | G09G 5/10 |
| | | | 345/690 |
| 2012/0127324 A1* | 5/2012 | Dickins | G09G 3/006 |
| | | | 348/191 |
| 2012/0206504 A1* | 8/2012 | Ha | G09G 3/3208 |
| | | | 345/690 |
| 2012/0229526 A1* | 9/2012 | Holmes | G09G 5/10 |
| | | | 345/690 |
| 2012/0269407 A1* | 10/2012 | Criminisi | G06T 7/77 |
| | | | 382/128 |
| 2013/0006532 A1* | 1/2013 | Sudo | G09G 5/06 |
| | | | 702/1 |
| 2013/0027418 A1* | 1/2013 | Tryndin | G06F 3/1415 |
| | | | 345/589 |
| 2013/0050504 A1* | 2/2013 | Safaee-Rad | G09G 5/02 |
| | | | 348/181 |
| 2013/0076777 A1* | 3/2013 | Park | G06F 3/14 |
| | | | 345/593 |
| 2013/0076899 A1* | 3/2013 | Eckelmann-Wendt | H04N 17/00 |
| | | | 348/143 |
| 2013/0107060 A1* | 5/2013 | Wei | G09G 3/36 |
| | | | 348/E17.005 |
| 2013/0187958 A1* | 7/2013 | Kimpe | G09G 3/3208 |
| | | | 345/690 |
| 2013/0287313 A1* | 10/2013 | Marchessoux | G06T 5/007 |
| | | | 382/274 |
| 2013/0307755 A1* | 11/2013 | Tomita | H04N 9/3185 |
| | | | 345/1.1 |
| 2013/0314549 A1* | 11/2013 | Higuchi | H04N 17/04 |
| | | | 348/175 |
| 2014/0232625 A1* | 8/2014 | Murase | G09G 3/2003 |
| | | | 345/89 |
| 2014/0232880 A1* | 8/2014 | Murase | H04N 17/02 |
| | | | 348/189 |
| 2014/0285532 A1* | 9/2014 | Yang | H04N 9/3182 |
| | | | 345/690 |
| 2014/0306979 A1* | 10/2014 | Chun | G09G 3/2003 |
| | | | 345/589 |
| 2014/0327360 A1* | 11/2014 | Hoshino | H05B 45/22 |
| | | | 315/151 |
| 2015/0092090 A1* | 4/2015 | Miura | A61B 1/00009 |
| | | | 348/242 |
| 2016/0073092 A1* | 3/2016 | Lin | G06T 7/85 |
| | | | 348/49 |
| 2016/0253455 A1* | 9/2016 | Hasegawa | G16H 30/40 |
| | | | 705/2 |
| 2016/0303453 A1* | 10/2016 | Kim | G09B 19/0038 |
| 2017/0118451 A1* | 4/2017 | Sakai | H04N 9/3147 |
| 2017/0184698 A1* | 6/2017 | Rueth | G09G 3/006 |
| 2017/0213524 A1* | 7/2017 | Tsunamoto | G09G 5/00 |
| 2017/0221405 A1* | 8/2017 | Yoshida | G09G 3/2007 |
| 2017/0223233 A1* | 8/2017 | Jung | H04N 5/202 |
| 2017/0333134 A1* | 11/2017 | Wollowick | G06T 7/70 |
| 2018/0332261 A1* | 11/2018 | Zhang | H04N 1/6044 |
| 2019/0052851 A1* | 2/2019 | Korl | H04N 5/247 |
| 2019/0122633 A1* | 4/2019 | Pan | G16H 30/20 |
| 2019/0124310 A1* | 4/2019 | Lai | H04N 9/3144 |
| 2019/0189083 A1* | 6/2019 | Lee | G09G 5/10 |
| 2019/0191150 A1* | 6/2019 | Zhang | G06T 7/0004 |
| 2019/0268590 A1* | 8/2019 | Kato | G06T 7/001 |
| 2020/0045277 A1* | 2/2020 | Hsiao | G06T 3/005 |
| 2020/0098303 A1* | 3/2020 | Kim | G09G 3/2044 |
| 2020/0175907 A1* | 6/2020 | Murase | G09G 3/20 |
| 2020/0211502 A1* | 7/2020 | Kim | G09G 3/006 |
| 2020/0265578 A1* | 8/2020 | Do | A61B 6/032 |
| 2021/0007574 A1* | 1/2021 | Hirayama | A61B 1/0661 |
| 2021/0142711 A1* | 5/2021 | Maeng | G09G 3/2003 |
| 2021/0241718 A1* | 8/2021 | Tsubokura | G09G 5/10 |

FOREIGN PATENT DOCUMENTS

| | | |
|---|---|---|
| TW | I504263 B | 10/2015 |
| TW | I667610 B | 8/2019 |

* cited by examiner

LUMINANCE CALIBRATION SYSTEM AND METHOD OF MOBILE DEVICE DISPLAY FOR MEDICAL IMAGES

BACKGROUND OF THE INVENTION

1. Field of the Invention

The present invention relates to a luminance calibration system and a method of a mobile device display, and more particularly, to a luminance calibration system and a method of a mobile device display for medical images.

2. Description of the Prior Art

Digital Imaging and Communications in Medicine (DICOM) defines file formats of medical images and network communication protocols, for processing, storing, printing and transmitting digital medical images. DICOM is a communication protocol based on TCP/IP to connect multiple network systems. For example, any system of medical instruments, servers, workstations, displays, printers, and network equipment that supports DICOM format may send and receive digital medical images and patient data through DICOM format files for integrating the above subsystems in medical picture archiving and communication system (PACS).

The DICOM also defines a standard of a grayscale standard display function (GSDF), which is used as a display specification that grayscale mobile devices need to comply with. However, the grayscale mobile devices on current markets are expensive and are fixed displays, which leads to low penetration rate and is not conducive to medical staff to instantly view medical images. For example, medical staff must go to a grayscale workstation to view medical images.

A trend nowadays is to integrate technology of medical displays into mobile devices with sufficient hardware specifications (such as smartphones and tablets) to increase the penetration rate and mobile convenience of medical image displays. However, the medical displays on the current markets do not consider impacts of ambient light sources on viewing the medical images with naked eyes, which affects the interpretation of the medical images by the medical staff. In practical applications, the luminous intensity of different light sources such as sunlight or artificial light equipment will affect results of viewing medical images with the naked eyes. For example, when the difference between the luminous intensity of the ambient light sources and the medical displays is too large, the medical images displayed by the medical displays cannot be clearly seen by the naked eyes, and the accuracy of the interpretation of the medical images is affected.

Therefore, in order to promote the accuracy of medical images interpretation, it is necessary to provide a system and a method for mobile luminance calibration.

SUMMARY OF THE INVENTION

It is therefore a primary objective of the present invention to provide a luminance calibration system and a method of s mobile device display for medical images.

The present invention discloses a luminance calibration system of a mobile device display for medical images, comprising a mobile device display, for transferring multiple original grayscale values; a photometer, for measuring multiple effective luminance values corresponding to the multiple original grayscale values; and a host, connecting to the mobile device display and the photometer, for executing a mobile luminance calibration process, wherein the mobile luminance calibration process comprises: connecting to the mobile device display to receive the multiple original grayscale values and to control the mobile device display to sequentially display multiple monochrome grayscale images corresponding to the multiple original grayscale values; connecting to the photometer to control the photometer to sequentially measure multiple effective luminance values corresponding to the multiple monochrome grayscale images and to receive the multiple effective luminance values from the photometer; calculating multiple original just-noticeable differences according to the multiple effective luminance values; calculating multiple calibrated grayscale values corresponding to the multiple original grayscale values according to a grayscale standard display function, the multiple original grayscale values, the multiple effective luminance values, and the multiple original just-noticeable differences; and transferring the multiple calibrated grayscale values to the mobile device display.

The present invention discloses a luminance calibration method of a mobile device display for medical images, using for a luminance calibration system of the mobile device display for medical images, wherein the luminance calibration system comprises a mobile device display, a photometer, and a host. The luminance calibration method is compiled into a code and stored in a built-in memory of the host. The luminance calibration method comprises: connecting to the mobile device display to receive the multiple original grayscale values and to control the mobile device display to sequentially display multiple monochrome grayscale images corresponding to the multiple original grayscale values, connecting to the photometer to control the photometer to sequentially measure multiple effective luminance values corresponding to the multiple monochrome grayscale images and to receive the multiple effective luminance values from the photometer, calculating multiple original just-noticeable differences according to the multiple effective luminance values, calculating multiple calibrated grayscale values corresponding to the multiple original grayscale values according to a grayscale standard display function, the multiple original grayscale values, the multiple effective luminance values, and the multiple original just-noticeable differences, and transferring the multiple calibrated grayscale values to the mobile device display.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
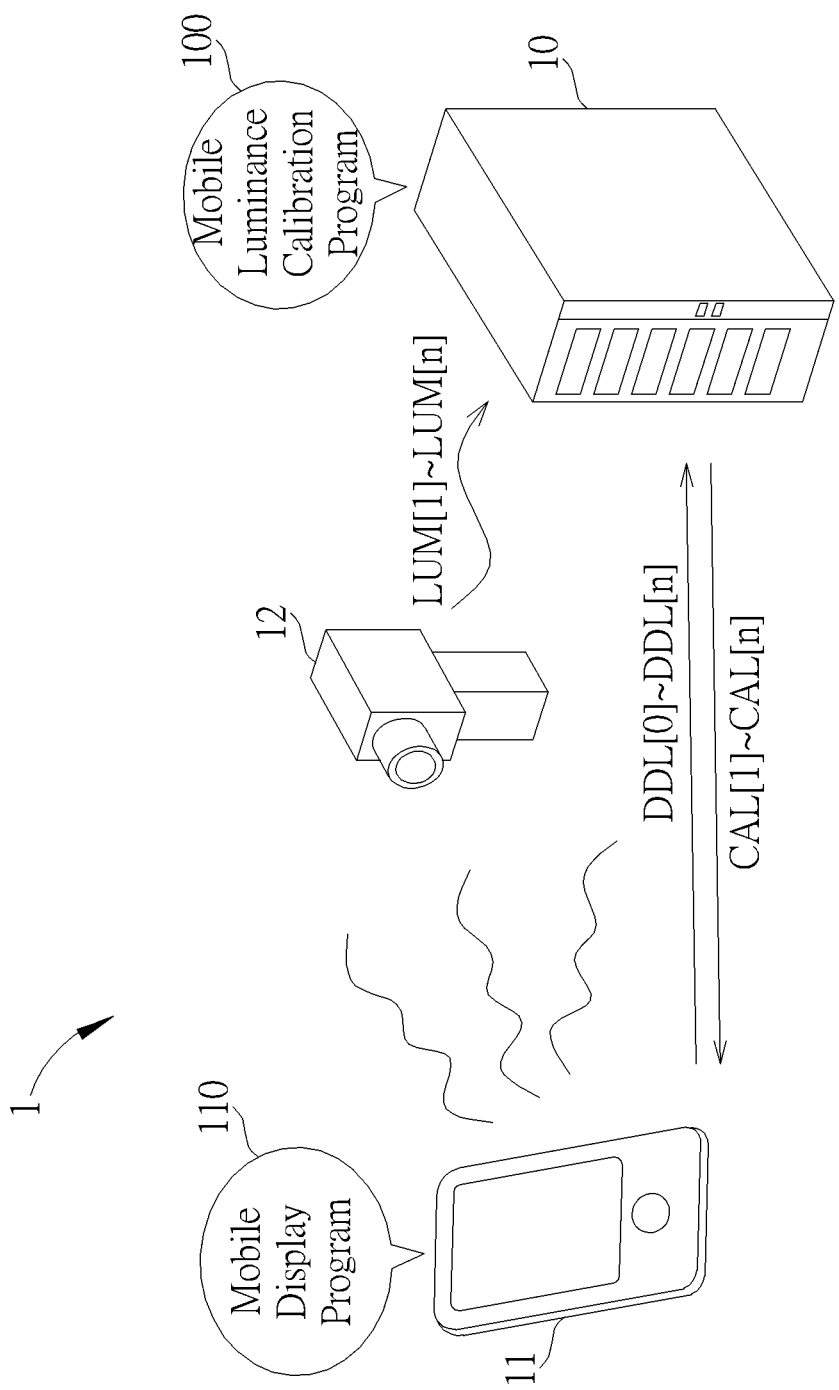
FIG. 1 is a schematic diagram of a calibration system according to an embodiment of the present invention.

FIG. 1 is a schematic diagram of a calibration system of a mobile device display for medical images (hereinafter referred to as calibration system 1) according to an embodiment of the present invention. The calibration system 1 comprises a host 10, a mobile device display 11, and a photometer 12. Suppose that the mobile device display 11 (such as a screen of a smart phone or a tablet) may be connected to the host 10 through wired or wireless communication. Suppose that an amount of original grayscale values DDL[0] to DDL[n] of the mobile device display 11 is 256 (where n is a positive integer from 0 to 255). The mobile device display 11 may execute a mobile display program 110 to transmit the original grayscale values DDL[0] to DDL[n] to the host 10 and to control the mobile device display 11 to sequentially display monochrome grayscale images corresponding to the original grayscale values DDL[0] to DDL[n]. A sensor of the photometer 12 faces the mobile device display 11 and may be connected to the host 10 through wired or wireless communication to measure multiple effective luminance values LUM[1] to LUM[n] corresponding to the original grayscale values DDL[0] to DDL[n], and transfers measured results to the host 10. It is worth noting that because the sensor of the photometer 12 will simultaneously receive light waves generated by the mobile device display 11 and ambient light sources, the multiple effective luminance values LUM[1] to LUM[n] measured by the photometer 12 may be used to describe luminous intensity of the mobile device display 11 plus the ambient light sources.

The host 10 (e.g., a desktop computer, a notebook computer, or a tablet computer) is used to execute a mobile luminance calibration program 100 to generate multiple calibrated grayscale values CAL[1] to CAL[n] corresponding to the multiple original grayscale values DDL[0] to DDL[n] of the mobile device display 11 according to the original grayscale values DDL[0] to DDL[n], the multiple effective luminance values LUM[1] to LUM[n], and a grayscale standard display function (GSDF). And the host 10 transfers the multiple calibrated grayscale values CAL[1] to CAL[n] to the mobile device display 11. In the embodiment, the GSDF complies with specifications defined by Digital Imaging and Communications in Medicine (DICOM). In this way, the mobile luminance calibration program 100 executed by the mobile device display 11 may receive the multiple calibrated grayscale values CAL[1] to CAL[n] to adjust the multiple original grayscale values DDL[0] to DDL[n] of the mobile device display 11, and allow the mobile device display 11 to display medical images according to the GSDF defined by the DICOM in the ambient light sources. For example, the medical images displayed by the mobile device display 11 have sufficient Just-Noticeable Difference (JND) for medical personnel to diagnose.

Figure 2:
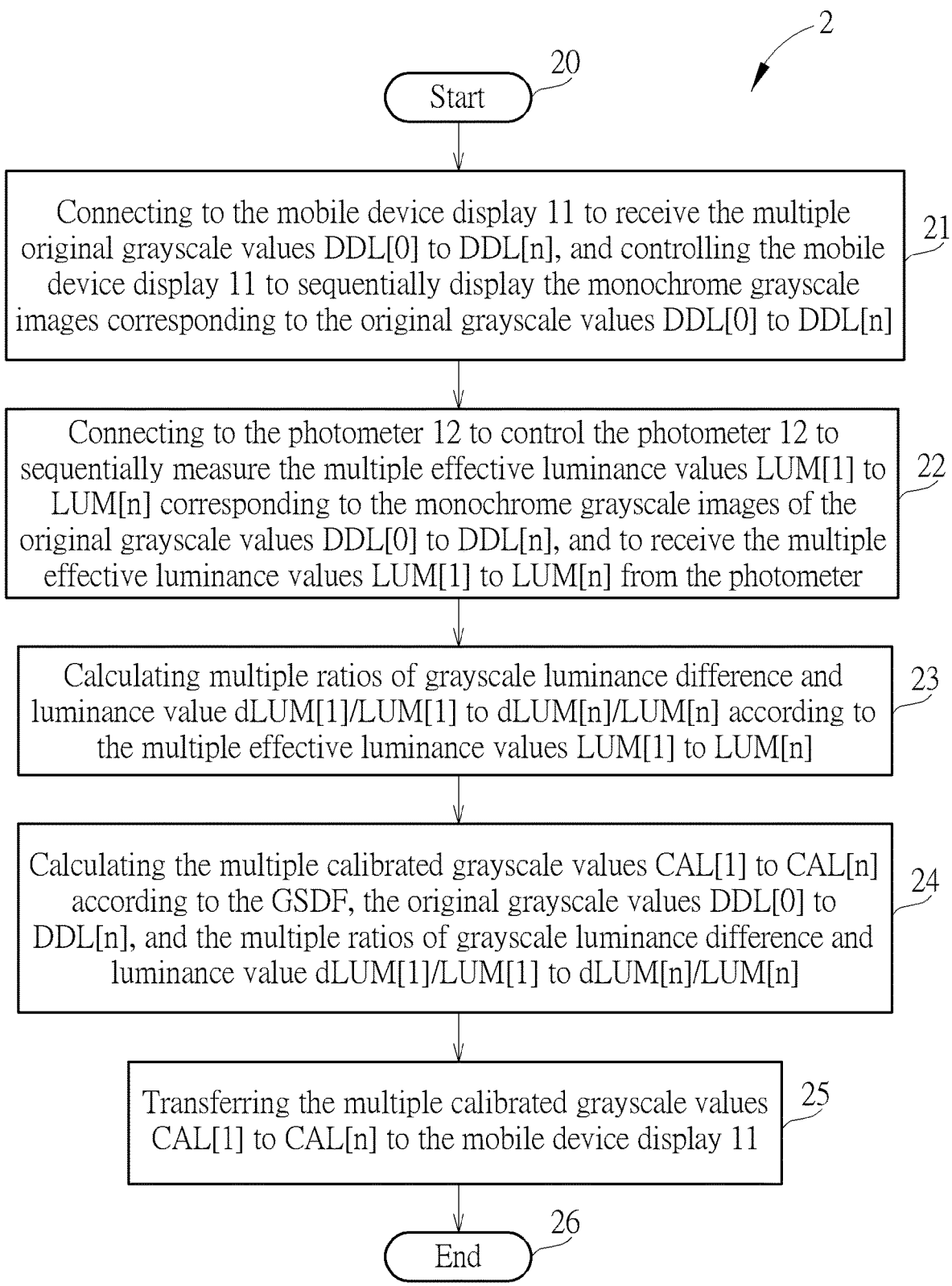
FIG. 2 is a flowchart of a mobile luminance calibration process according to the embodiment of the present invention.
Figure 3:
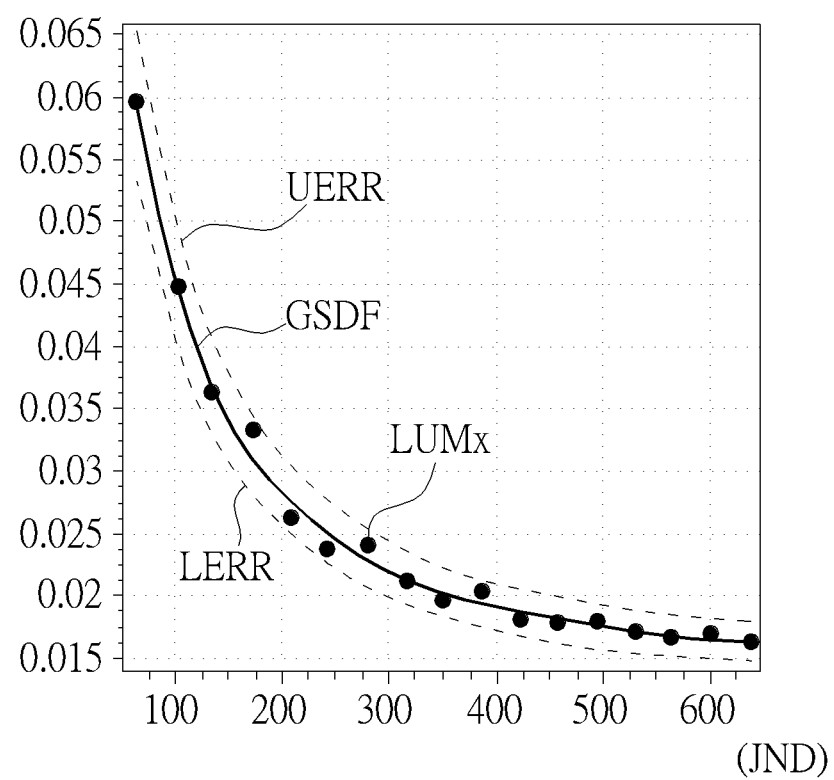
FIG. 3 is a calibration graph of just-noticeable difference to grayscale luminance according to the embodiment of the present invention.
Figure 4:
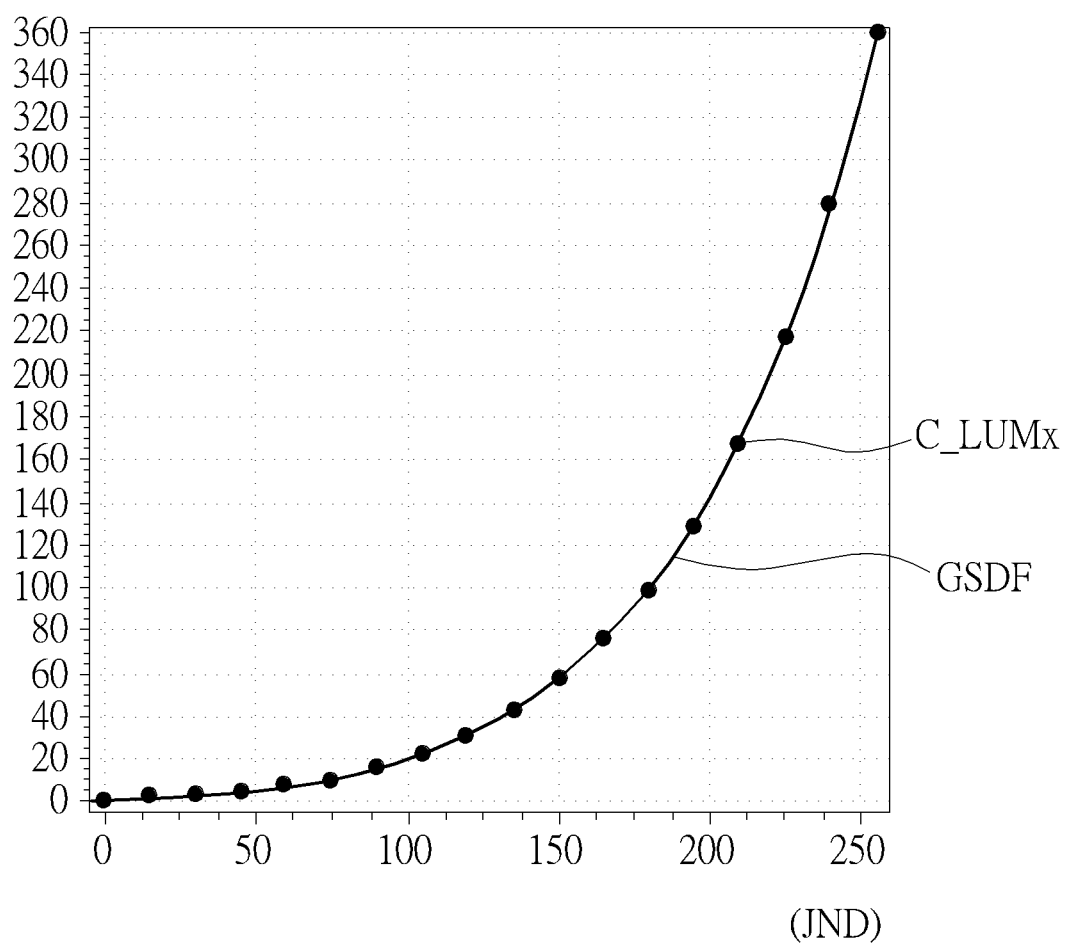
FIG. 4 is a calibration grayscale graph of a mobile device display according to the embodiment of the present invention.

An operation method of the calibration system 1 may be summarized as a mobile luminance calibration process 2, as shown in FIG. 2. FIG. 3 is a calibration graph of the just-noticeable difference to grayscale luminance of the embodiment of the present invention. FIG. 4 is a calibration grayscale graph of the mobile device display 11 of the embodiment of the present invention. In order to explain the mobile luminance calibration process 2, please refer to FIG. 2, FIG. 3 and FIG. 4 at the same time. The mobile luminance calibration process 2 may be compiled into the mobile luminance calibration program 100 and stored in a built-in memory of the host 10, and used to instruct the host 10 to execute following steps.

Step 20: Start.

Step 21: Connecting to the mobile device display 11 to receive the multiple original grayscale values DDL[0] to DDL[n], and controlling the mobile device display 11 to sequentially display the monochrome grayscale images corresponding to the original grayscale values DDL[0] to DDL[n].

Step 22: Connecting to the photometer 12 to control the photometer 12 to sequentially measure the multiple effective luminance values LUM[1] to LUM[n] corresponding to the monochrome grayscale images of the original grayscale values DDL[0] to DDL[n], and to receive the multiple effective luminance values LUM[1] to LUM[n] from the photometer 12.

Step 23: Calculating multiple ratios of grayscale luminance difference and luminance value dLUM[1]/LUM[1] to dLUM[n]/LUM[n] according to the multiple effective luminance values LUM[1] to LUM[n].

Step 24: Calculating the multiple calibrated grayscale values CAL[1] to CAL[n] according to the GSDF, the original grayscale values DDL[0] to DDL[n], and the multiple ratios of grayscale luminance difference and luminance value dLUM[1]/LUM[1] to dLUM[n]/LUM[n].

Step 25: Transferring the multiple calibrated grayscale values CAL[1] to CAL[n] to the mobile device display 11.

Step 26: End.

In Step 21, the host 10 may connect to the mobile device display 11 to receive the multiple original grayscale values DDL[0] to DDL[n] and control the mobile device display 11 to sequentially display the multiple monochrome grayscale images corresponding to the multiple original grayscale values DDL[0] to DDL[n. In Step 22, the host 10 may connect to the photometer 12 to control the photometer 12 to sequentially measure the multiple effective luminance values LUM[1] to LUM[n] corresponding to the monochrome grayscale images of the original grayscale values DDL[0] to DDL[n], and to receive the multiple effective luminance values LUM[1] to LUM[n] from the photometer 12.

In Step 23, the host 10 may calculate the multiple ratios of grayscale luminance difference and luminance value dLUM[1]/LUM[1] to dLUM[n]/LUM[n] according to the multiple effective luminance values LUM[1] to LUM[n], wherein LUM[x] is one effective luminance value among the multiple effective luminance values LUM[1] to LUM[n] (1≤x≤n, 0≤n≤255). A vertical axis of the FIG. 3 is the ratio of grayscale luminance difference and luminance value dLUM[x]/LUM[x] (where dLUM[x]=LUM[x]−LUM[x−1]), and a horizontal axis is unit levels that may be distinguished by naked eyes (e.g., 640 unit levels). In an embodiment, and in FIG. 3, a maximum allowable error curve UERR and a minimum allowable error curve LERR may be set in the mobile luminance calibration program 100, which are represented by dotted lines. A difference between the allowable error curve and the GSDF curve of DICOM is between +10% and −10%, but not limited thereto. When the ratio of grayscale luminance difference and luminance value dLUM[x]/LUM[x] exceeds a range of the maximum allowable error curve UERR and the minimum allowable error curve LERR, a closest maximum or minimum allowable error value is used to determine the ratio of grayscale luminance difference and luminance value, but not limited thereto.

In Step 24, the host 10 may calculate the multiple calibrated grayscale values CAL[1] to CAL[n] according to the GSDF, the original grayscale values DDL[0] to DDL[n], and the multiple original JND, wherein the multiple original JND may be expressed as the ratios of grayscale luminance difference and luminance value dLUM[1]/LUM[1] to dLUM[n]/LUM[n]. In detail, the host 10 may determine an equivalent unit level of each of the original grayscale values DDL[0] to DDL[n] in 640 JND defined by the GSDF according to 640 unit levels of the JND defined by the GSDF and 256 gray levels of the mobile device display 11. For example, the equivalent unit levels corresponding to the original grayscale values DDL[0] to DDL[n] in the JND defined by the GSDF, which are 0, 2.51, 5.02, . . . , 637.50, 640, etc. Next, the host 10 may find multiple standard luminance values of the equivalent unit levels 0, 2.51, 5.02, . . . , 637.50, 640 corresponding to the original grayscale values DDL[0] to DDL[n], wherein the multiple standard luminance values are specified in the JND defined by the GSDF, and the host 10 may calculate the multiple calibrated grayscale values CAL[1] to CAL[n] by comparing the multiple standard luminance values with the multiple effective luminance values LUM[1] to LUM[n]. Taking the original grayscale value DDL[110] as an example, the equivalent unit level of the original grayscale value DDL[110] in the JND defined by the GSDF is 276.08. As shown in FIG. 3, when the ratio of grayscale luminance difference and luminance value dLUM[110]/LUM[110] is greater than a standard value of the GSDF curve, it means that the effective luminance value LUM[110] displayed by the mobile device display 11 under the setting of the original grayscale value DDL[110] is too large, so the mobile device display 11 must reduce the effective luminance value LUM[110] according to the calibrated grayscale value CAL[110] to comply with the GSDF curve of the DICOM. Conversely, when the ratio of grayscale luminance difference and luminance value dLUM[110]/LUM[110] is smaller than the standard value of the GSDF curve, it means that the effective luminance value LUM[110] displayed by the mobile device display 11 under the setting of the original grayscale value DDL[110] is too small, so the mobile device display 11 must increase the effective luminance value LUM[110] according to the calibrated grayscale value CAL[110] to comply with the GSDF curve of the DICOM.

In Step 25, the host 10 may transfer the multiple calibrated grayscale values CAL[1] to CAL[n] to the mobile device display 11, which allows the medical images displayed by the mobile device display 11 to comply with the GSDF curve of the DICOM. As shown in FIG. 4, the mobile device display 11 may display multiple calibrated luminance values C_LUM[1] to C_LUM[n] according to the multiple calibrated grayscale values CAL[1] to CAL[n], wherein C_LUM[x] is used to indicate any of the multiple calibrated luminance values C_LUM[1] to C_LUM[n]. In an embodiment, the host 10 may convert the multiple calibrated grayscale values CAL[1] to CAL[n] into a mobile grayscale versus luminance calibration curve, and pack the mobile grayscale versus luminance calibration curve into a single transmission packet to the mobile device display 11, but not limited thereto.

Figure 5:
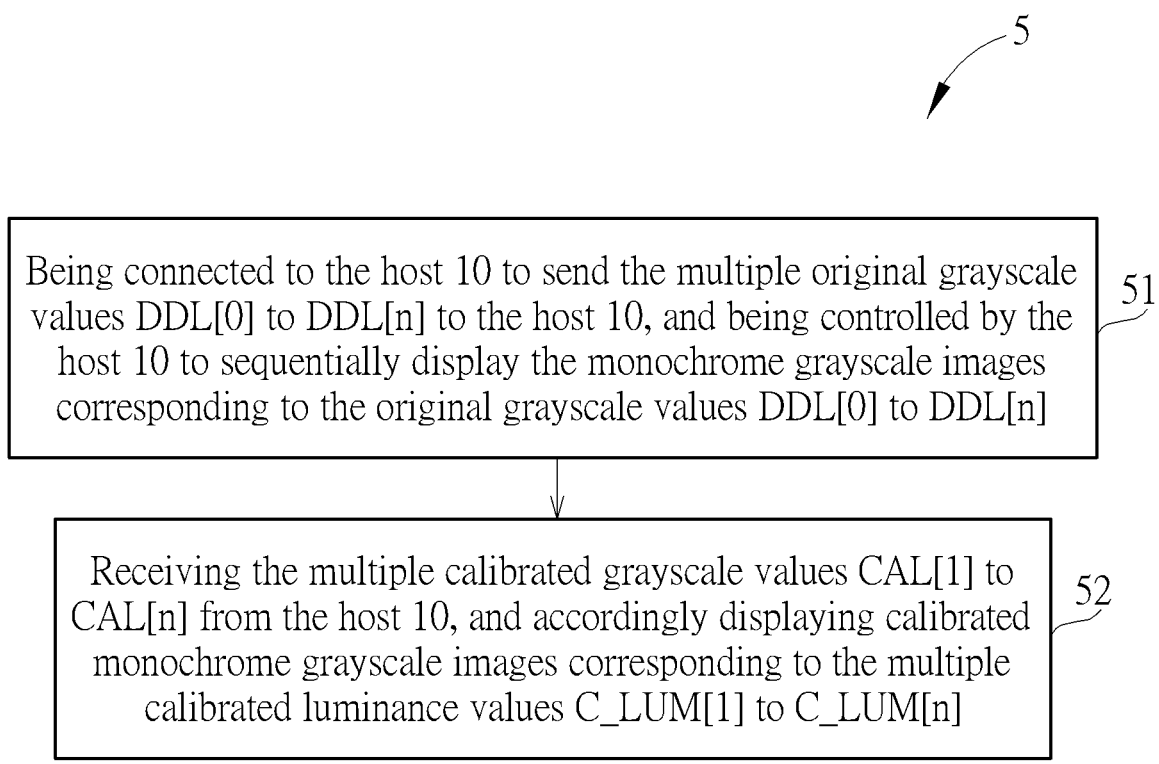
FIG. 5 is a flowchart of a mobile display process according to the embodiment of the present invention.

An operation method of the mobile device display 11 may be summarized as a mobile display process 5, as shown in FIG. 5. The mobile display process 5 may be compiled into the mobile display program 110 and stored in the built-in memory of the host 10, and used to instruct the host 10 to execute following steps.

Step 51: Being connected to the host 10 to send the multiple original grayscale values DDL[0] to DDL[n] to the host 10, and being controlled by the host 10 to sequentially display the monochrome grayscale images corresponding to the original grayscale values DDL[0] to DDL[n].

Step 52: Receiving the multiple calibrated grayscale values CAL[1] to CAL[n] from the host 10, and accordingly displaying calibrated monochrome grayscale images corresponding to the multiple calibrated luminance values C_LUM[1] to C_LUM[n].

In Step 51, the mobile device display 11 may be connected to the host 10 to transmit the multiple original grayscale values DDL[0] to DDL[n] to the host 10, and controlled by the host 10 to sequentially display the monochrome grayscale images corresponding to the original grayscale values DDL[0] to DDL[n]. After the host 10 executes the mobile luminance calibration process 2, in Step 52, the mobile device display 11 may receive the multiple calibrated grayscale values CAL[1] to CAL[n] from the host 10, and accordingly display the calibrated monochrome grayscale images corresponding to the multiple calibrated luminance values C_LUM[1] to C_LUM[n].

It is worth noting that the mobile luminance calibration program 100 executed by the host 10 and the mobile display program 110 executed by the mobile device display 11 will only adjust the medical images within their operating windows, and will not change the images outside their operating windows.

Since the original grayscale settings of the display are kept, the mobile display program 110 only adjusts the medical images within its operating window, and does not affect the images outside its operating window. In this way, the mobile luminance calibration program 100 and the coordinated mobile display program 110 not only allow the mobile device display 11 to be used as a medical screen, but also retain functions used by a general screen.

In summary, the present invention provides a luminance calibration system and a method of a mobile device display for medical images, so that the mobile device display may display medical images according to the GSDF defined by the DICOM in its ambient light sources. For example, the medical images displayed by the mobile device display have sufficient just-noticeable difference (JND) for medical personnel to diagnose. Furthermore, the luminance calibration system and the method of the mobile device display for medical images of the present invention will only adjust medical images within its operating window, without affecting images outside its operating window. In this way, the luminance calibration system and the method of the mobile device display for medical images of the present invention not only allow the mobile device display to be used as a medical screen, but also retain functions used by a general screen.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A luminance calibration system of a mobile device display for medical images, comprising:
    a mobile device display, for transferring multiple original grayscale values;
    a photometer, for measuring multiple effective luminance values corresponding to the multiple original grayscale values; and a host, connecting to the mobile device display and the photometer, for executing a mobile luminance calibration process, wherein the mobile luminance calibration process comprises:

the host connecting to the mobile device display to receive the multiple original grayscale values from the mobile device display and to control the mobile device display to sequentially display multiple monochrome grayscale images corresponding to the multiple original grayscale values;

connecting to the photometer to control the photometer to sequentially measure multiple effective luminance values corresponding to the multiple monochrome grayscale images and to receive the multiple effective luminance values from the photometer;

calculating multiple original just-noticeable differences according to the multiple effective luminance values, wherein one of the multiple original just-noticeable differences larger than a maximum allowable error curve or smaller than a minimum allowable error curve is set to be equal to a maximum allowable error value of the maximum allowable error curve or a minimum allowable error value of the minimum allowable error curve;

calculating multiple calibrated grayscale values corresponding to the multiple original grayscale values according to a grayscale standard display function (GSDF), the multiple original grayscale values, the multiple effective luminance values, and the multiple original just-noticeable differences, wherein the step of calculating the multiple calibrated grayscale values corresponding to the multiple original grayscale values according to the grayscale standard display function, the multiple original grayscale values, the multiple effective luminance values, and the multiple original just-noticeable differences comprises:

according to a total number of multiple standard distinguishable difference unit levels of the grayscale standard display function and a total number of the multiple original grayscale values, respectively determining multiple equivalent unit levels of the multiple original grayscale values in the multiple standard distinguishable difference unit levels;

finding multiple standard luminance values corresponding to the multiple equivalent unit levels in the grayscale standard display function; and comparing the standard luminance values with the multiple effective luminance values, respectively, and calculating the multiple calibrated grayscale values corresponding to the multiple original grayscale values; and transferring the multiple calibrated grayscale values to the mobile device display.

2. The luminance calibration system of claim 1, wherein one of the multiple original just-noticeable differences is expressed as:

dLUM[x]/LUM[x], dLUM[x] is LUM[x]−LUM[x−1], wherein LUM[x] is a first effective luminance value among the multiple effective luminance values, LUM[x−1] is a second effective luminance value among the multiple effective luminance values, $1 \leq x \leq n$, $0 \leq n$, n is a total number of the multiple original grayscale values, and n, x are integers.

3. The luminance calibration system of claim 1, wherein the step of transferring the multiple calibrated grayscale values to the mobile device display comprises:

converting the multiple calibrated grayscale values into an mobile grayscale versus luminance calibration curve; and packaging the mobile grayscale versus luminance calibration curve into a single transmission packet to the mobile device display.

4. A luminance calibration method of a mobile device display for medical images, using for a luminance calibration system of the mobile device display for medical images, wherein the luminance calibration system of the mobile device display for medical images comprises the mobile device display, a photometer, and a host, the luminance calibration method of the mobile device display for medical images is compiled into a code and stored in a built-in memory of the host, and comprises:

the host connecting to the mobile device display to receive the multiple original grayscale values from the mobile device display and to control the mobile device display to sequentially display multiple monochrome grayscale images corresponding to the multiple original grayscale values;

connecting to the photometer to control the photometer to sequentially measure multiple effective luminance values corresponding to the multiple monochrome grayscale images and to receive the multiple effective luminance values from the photometer;

calculating multiple original just-noticeable differences according to the multiple effective luminance values, wherein one of the multiple original just-noticeable differences larger than a maximum allowable error curve or smaller than a minimum allowable error curve is set to be equal to a maximum allowable error value of the maximum allowable error curve or a minimum allowable error value of the minimum allowable error curve;

calculating multiple calibrated grayscale values corresponding to the multiple original grayscale values according to a grayscale standard display function, the multiple original grayscale values, the multiple effective luminance values, and the multiple original just-noticeable differences, wherein the step of calculating the multiple calibrated grayscale values corresponding to the multiple original grayscale values according to the grayscale standard display function, the multiple original grayscale values, the multiple effective luminance values, and the multiple original just-noticeable differences comprises:

according to a total number of multiple standard distinguishable difference unit levels of the grayscale standard display function and a total number of the multiple original grayscale values, respectively determining multiple equivalent unit levels of the multiple original grayscale values in the multiple standard distinguishable difference unit levels;

finding multiple standard luminance values corresponding to the multiple equivalent unit levels in the grayscale standard display function; and comparing the standard luminance values with the multiple effective luminance values, respectively, and calculating the multiple calibrated grayscale values corresponding to the multiple original grayscale values; and transferring the multiple calibrated grayscale values to the mobile device display.

5. The luminance calibration method of claim 4, wherein one of the multiple original just-noticeable differences is expressed as:

dLUM[x]/LUM[x], dLUM[x] is LUM[x]−LUM[x−1], wherein LUM[x] is a first effective luminance value among the multiple effective luminance values, LUM[x−1] is a second effective luminance value among the multiple effective luminance values, 1≤x≤n, 0≤n, n is a total number of the multiple original grayscale values, and n, x are integers.

6. The luminance calibration method of claim 4, wherein the step of transferring the multiple calibrated grayscale values to the mobile device display comprises:

converting the multiple calibrated grayscale values into an mobile grayscale versus luminance calibration curve; and packaging the mobile grayscale versus luminance calibration curve into a single transmission packet to the mobile device display.

7. The luminance calibration system of claim 1, wherein the mobile device display adjusts the medical images within an operating window of the mobile device display according to the multiple calibrated grayscale values, and maintaining images outside the operating window according to the multiple original grayscale values.

\* \* \* \* \*